United States Patent
Kung

(10) Patent No.: US 7,069,769 B2
(45) Date of Patent: Jul. 4, 2006

(54) ULTRAVIOLET PHOTOACOUSTIC OZONE DETECTION

(75) Inventor: Andy Kung, Taipei (TW)

(73) Assignee: Academia Sinica, Taipei (TW)

( * ) Notice: Subject to any disclaimer, the term of this patent is extended or adjusted under 35 U.S.C. 154(b) by 85 days.

(21) Appl. No.: 10/760,633

(22) Filed: Jan. 20, 2004

(65) Prior Publication Data
US 2005/0160791 A1 Jul. 28, 2005

(51) Int. Cl.
G01N 21/00 (2006.01)

(52) U.S. Cl. .......... 73/24.02; 73/23.2

(58) Field of Classification Search ............ 73/24.02, 73/23.2
See application file for complete search history.

(56) References Cited

U.S. PATENT DOCUMENTS

| | | | |
|---|---|---|---|
| 4,197,009 A * | 4/1980 | Berry et al. ............ | 356/301 |
| 5,151,590 A * | 9/1992 | Takamoto et al. ...... | 250/215 |
| 5,913,234 A * | 6/1999 | Julliard et al. ......... | 73/24.02 |
| 6,662,627 B1 * | 12/2003 | Arnott et al. ........... | 73/24.02 |
| 6,694,799 B1 * | 2/2004 | Small ..................... | 73/24.02 |
| 2003/0159498 A1 * | 8/2003 | Small ..................... | 73/24.02 |

OTHER PUBLICATIONS

Jun-Ying Zhang et al. "Efficient Xel* excimer ultraviolet sources from a dielectric barrier discharge". Journal of Applied Physics 84(3):1174-1178, Aug. 1, 1998.

M. Nägele et al. "Mobile laser spectrometer with novel resonant multipass photoacoustic cell for trace-gas sensing". Applied Physics B 70:895-901, 2000.

Edjar M. Telles et al. "A photoacoustic spectrometer for ozone detection". Instrum. Sci. Tech. 26:157-175, 1998.

Geng-Chiau Liang et al. "Photoacoustic Trace Detection of Methane Using Compact Solid-State Lasers". J. Phys. Chem A 104:10179-10183, 2000.

Frank McElroy et al. "Determination of Ozone by Ultraviolet Analysis". Final Draft: For addition into US EPA Quality Assurance Handbook for Air Pollution Measurement Systems, 1997.

* cited by examiner

Primary Examiner—Hezron Williams
Assistant Examiner—Rodney Frank
(74) Attorney, Agent, or Firm—Fish & Richardson P.C.

(57) ABSTRACT

A photoacoustic ozone detector includes an acoustic chamber, an ultraviolet light source, and a detector to detect audio signals. The acoustic chamber has an inlet for receiving a gas mixture containing ozone and an outlet for removing the gas mixture from the chamber. The ultraviolet light source generates ultraviolet light having wavelengths shorter than 400 nm, and the ultraviolet light is modulated at a modulation frequency substantially equal to a resonant frequency of the acoustic chamber. The ultraviolet light source is positioned relative to the acoustic chamber so that the ultraviolet light passes through the gas mixture in the acoustic chamber. The detector detects an audio signal in the acoustic chamber having a frequency substantially equal to the modulation frequency of the ultraviolet light. A signal processor generates an output indicative of a concentration of the ozone in the gas mixture based on the detected audio signal.

21 Claims, 4 Drawing Sheets

ULTRAVIOLET PHOTOACOUSTIC OZONE DETECTION

BACKGROUND

This invention relates to ultraviolet photoacoustic detection, and more particularly to ultraviolet photoacoustic zone detection.

Ozone is a strong oxidizing agent. An appropriate amount of ozone can be used to kill germs and bacteria and to remove toxic chemicals from fruits and vegetables. However, too much ozone can cause damage to the environment and cause harm to humans.

One method of detecting ozone is to intermix ozone with another gas and detect the chemiluminescence that results from the chemical reaction of the two gases. Another method is to expose ozone to ultraviolet light and measure the amount of reduction in the intensity of ultraviolet light at 254 nm. A higher concentration of ozone results in a greater absorption of the ultraviolet light. Such ultraviolet light can be generated from HgI lamps, which emit light having a wavelength of 253.7 nm.

When ultraviolet absorption is used for ozone detection, components in the air, such as water vapor and aromatic hydrocarbon compounds, may interfere the absorption process. Water does not absorb at 254 nm, but when the humidity is high, condensation of water vapor can block the passage of ultraviolet light and affect the accuracy of the measurement. Volatile aromatic compounds, such as benzene, toluene, xylene, and their derivatives that are generated by the combustion of fossil fuels, have absorption bands that overlaps with ozone at 254 nm. One way to overcome this is to use scrubbers to remove the aromatic compounds. Another way is to make a first ultraviolet absorption measurement, use scrubbers to remove the ozone, make another ultraviolet absorption measurement, and compare the difference in measurements.

SUMMARY

In a general aspect, this invention features a photoacoustic ozone detector that includes an acoustic chamber, an ultraviolet light source, and at least one microphone. The acoustic chamber has an inlet for receiving a gas mixture containing ozone and an outlet for removing the gas mixture from the chamber. The ultraviolet light source generates ultraviolet light having wavelengths shorter than 400 nm, and the ultraviolet light is modulated at a modulation frequency substantially equal to a resonant frequency of the acoustic chamber. The ultraviolet light source is positioned relative to the acoustic chamber so that the ultraviolet light passes through the gas mixture in the acoustic chamber. At least one microphone detects an audio signal in the acoustic chamber having a frequency substantially equal to the modulation frequency of the ultraviolet light.

This and other aspects of the invention include one or more of the following features. In the photoacoustic ozone detector, the ultraviolet light source is selected to have an emission spectrum with full width at half maximum greater than 1 nm.

The photoacoustic ozone detector includes a signal processor to generate an output indicative of a concentration of the ozone in the gas mixture based on the detected audio signal. The photoacoustic ozone detector includes a photodetector to detect a level of the ultraviolet light passing through the acoustic chamber, and the signal processor uses the level of the ultraviolet light to normalize the output indicative of the concentration of the ozone.

The acoustic chamber includes two tubes, the ultraviolet light passing through one of the tubes. A microphone is attached to each tube, and a signal processor generates an output indicative of a concentration of the ozone in the gas mixture based on a difference in the audio signals detected by the microphones.

The acoustic chamber has two ends, each coupled to an acoustic filter to reduce background noise having a frequency substantially equal to the resonant frequency. The acoustic filter includes a quarter wavelength acoustic filter.

The ultraviolet light source includes an electric discharge lamp. The electric discharge lamp includes xenon gas and iodine gas. The ultraviolet light source generates ultraviolet light having wavelengths between 240 nm to 270 nm. The light source includes a lens or a lens reflector to concentrate the ultraviolet light into the acoustic chamber.

The acoustic chamber is selected to have dimensions so that the resonant frequency is between 100 Hz to 40 kHz.

In another general aspect, this invention features an apparatus that includes an acoustic chamber to receive a gas mixture, a light source having an emission spectrum having at least one emission peak with a full width at half maximum greater than 1 nm, the light source emitting light that is modulated at a frequency substantially equal to a resonant frequency of the chamber, and a detector to detect a signal indicative of absorption of the modulated light by a gas component in the gas mixture, the signal having a frequency substantially equal to the modulation frequency of the light.

This and other aspects of the invention include one or more of the following features. The gas mixture includes ozone ($O_3$), and the light source generates ultraviolet light comprising light waves having wavelengths between 240 nm to 270 nm.

The apparatus of claim 13 in which the gas mixture includes sulfur dioxide ($SO_2$), and the light source generates light comprising light waves having wavelengths between 270 nm to 310 nm.

The gas mixture includes nitric dioxide ($NO_2$), and the light source generates light comprising light waves having wavelengths between 350 nm to 450 nm.

The apparatus includes a signal processor to generate an output indicative of a concentration of gas component in the gas mixture based on the detected signal.

The modulated ultraviolet light source emits ultraviolet light that has components having wavelengths between 237 nm and 275 nm.

The modulation frequency is substantially equal to a resonant frequency of the chamber.

The acoustic chamber is configured to have a dimension so that the resonant frequency is between 100 Hz to 40 kHz.

The apparatus includes an acoustic filter attached to an end of the chamber to reduce background noise having a frequency substantially equal to a modulation frequency of the light emitted from the light source.

The apparatus includes a gas handling system to supply the gas mixture.

In a general aspect, this invention features an apparatus that includes a first resonator tube to receive a portion of a gas mixture, a second resonator tube to receive another portion of the gas mixture, the first and second resonator tubes having a common resonant frequency. The apparatus includes a first microphone to generate a first output representing acoustic signals in the first resonator tube, and a second microphone to generate a second output representing acoustic signals in the second resonator tube. The apparatus includes a light source having an emission spectrum broader than 1 nm near a predetermined wavelength, the light source emitting light that is modulated at a frequency substantially equal to the resonant frequency, the light passing through the first resonator tube. The apparatus includes a signal processor to determine a difference between the first and second outputs to generate a differential output having a frequency substantially equal to the modulation frequency.

This and other aspects of the invention include one or more of the following features. The apparatus includes a gas handling system to supply the gas mixture.

In another general aspect, the invention features a method of detecting ozone in a gas mixture by passing a modulated ultraviolet light through a photoacoustic chamber containing the gas mixture. Microphones detect audio signals generated from changes in the gas pressure caused by ozone absorbing the modulated light. The audio signals are processed to determine the amount of ozone in the gas mixture.

In another general aspect, this invention features a method that includes detecting ozone in a gas mixture in an acoustic chamber irradiated with ultraviolet light that is modulated at a frequency that is substantially equal to a resonant frequency of the acoustic chamber, including measuring a signal representing changes in a pressure of the gas mixture, the signal having a frequency substantially equal to the modulation frequency of the ultraviolet light, the ultraviolet light having an emission spectrum with a full width at half maximum greater than 1 nm, the ultraviolet light having components with wavelengths less than 400 nm.

This and other aspects of the invention include one or more of the following features. The modulation frequency of the ultraviolet light is between 100 Hz to 40 kHz.

The method includes normalizing the signal based on a detected level of ultraviolet light passing through the acoustic chamber. The method includes generating an output indicative of a concentration of the ozone in the gas mixture based on an amplitude of the normalized signal.

The method includes generating the ultraviolet light using an electric discharge lamp.

The acoustic chamber includes two resonator tubes, each corresponding to a microphone, the ultraviolet light passing through only one of the tubes. Measuring the signal representing changes in the pressure of the gas mixture includes determining a difference between audio signals measured by the two microphones.

In another general aspect, this invention features a method that includes supplying a gas mixture to a chamber, the gas mixture containing a gas component to be detected, generating light waves from a light source having an emission spectrum with at least one emission peak having a full width at half maximum greater than 1 nm, modulating the light wave at a modulation frequency corresponding to a resonant frequency of the chamber, passing the modulated light waves through the chamber, detecting a signal having a frequency substantially equal to the modulation frequency, and generating an output indicative of a concentration of the gas component.

This and other aspects of the invention include one or more of the following features. The gas component includes ozone. The light waves have components having wavelengths between 235 nm and 275 nm. The modulation frequency is substantially equal to a resonant frequency of the chamber. The resonant frequency of the chamber is between 100 Hz to 40 kHz.

The method includes detecting an intensity of the ultraviolet light after passing through the chamber, and normalizing the output indicative of the concentration of the ozone based on the intensity of the ultraviolet light.

The method includes filtering background noise by using acoustic quarter wave filters to increase the signal-to-noise ratio of the signal having a frequency substantially equal to the modulation frequency.

In another general aspect, this invention features a method that includes receiving a portion of a gas mixture at a first resonator tube, and receiving another portion of the gas mixture at a second resonator tube, the first and second resonator tubes having a common resonant frequency. The method includes passing light through the first resonator tube, the light generated from a light source having an emission spectrum broader than 1 nm near a predetermined wavelength, the light being modulated at a frequency substantially equal to the resonant frequency. The method includes detecting a first acoustic signal in the first resonator tube, detecting a second acoustic signal in the second resonator tube, and determining a difference between the first and second acoustic signals.

Other features and advantages of the invention are apparent from the following description, and from the claims.

DESCRIPTION

Figure 1:
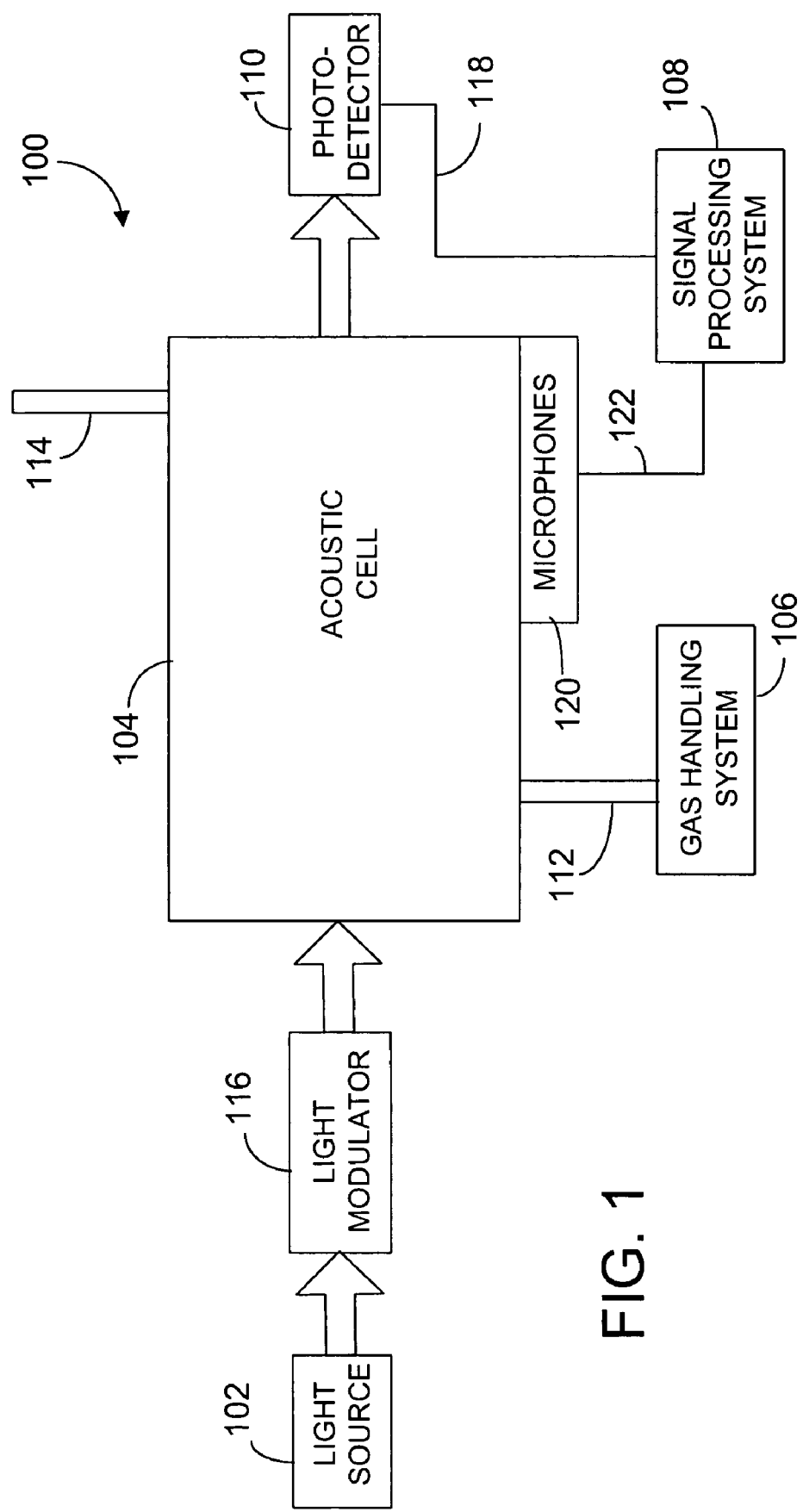
FIG. 1 depicts a photoacoustic ozone detector.

Referring to FIG. 1, an ultraviolet photoacoustic ozone detector 100 includes a broadband ultraviolet light source 102, a photoacoustic cell 104, a gas handling system 106, a photodetector 110, and an electronic signal processing system 108. A gas mixture containing ozone is supplied by the gas handling system 106, enters the photoacoustic cell 104 through a gas inlet 112, and exits the photoacoustic cell 104 through a gas outlet 114. When the ultraviolet light is absorbed by the ozone molecules, the absorbed light is converted to heat, causing changes in the pressure of the gas mixture. A light modulator 116 modulates the ultraviolet light reaching the photoacoustic cell with a modulating frequency equal to the resonance frequency of the photoacoustic cell 104. Absorption of the ultraviolet light by the ozone creates modulated changes in the gas pressure, resulting in a sound wave having a frequency equal to the modulation frequency of the photoacoustic cell. The amplitude of the sound wave signal is proportional to the amount of light absorbed, which is indicative of the concentration of ozone in the gas mixture. The sound wave signal is amplified by the photoacoustic cell (due to its resonant characteristics), allowing small amounts of ozone to be detected.

Figure 6:
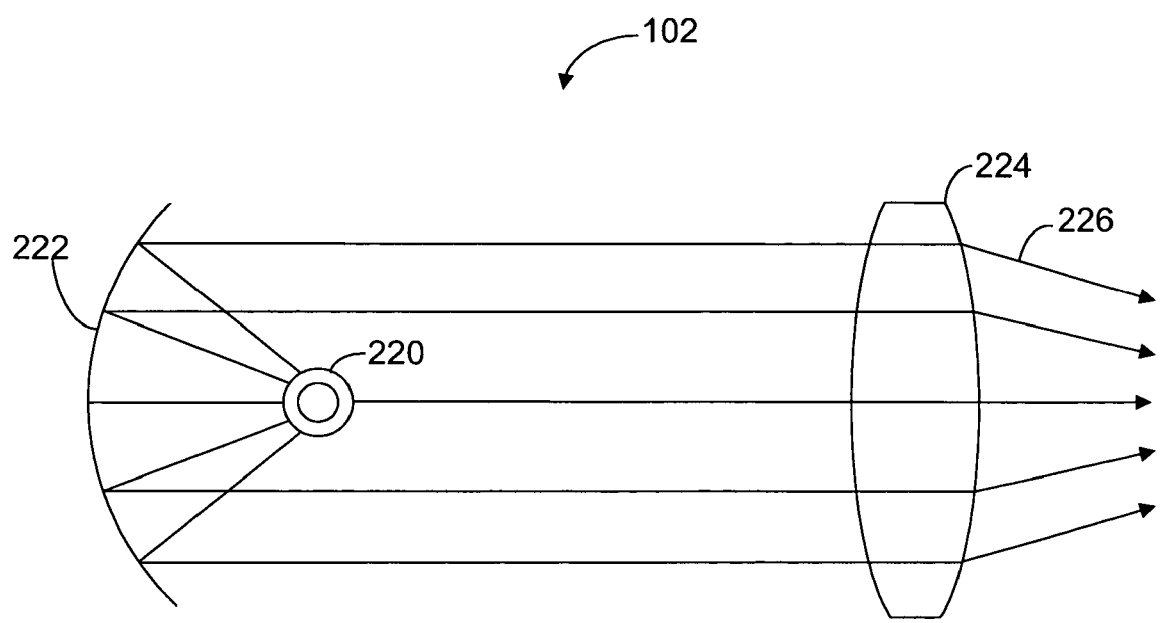
FIG. 6 depicts an electric discharge lamp light source.

The broadband ultraviolet light source 102 has an emission spectrum that overlaps the absorption spectrum of ozone molecules. The light source 102 is selected to have an emission spectrum having a full width at half maximum greater than, for example, 1 nm. In one example, the light source 102 contains an electric discharge lamp 220 (see FIG. 6) that contains xenon gas mixed with a small amount of iodine gas. The gas mixture emits ultraviolet light waves with wavelengths having a larger portion between 240 nm to 270 nm, with an emission peak near 253 nm. The emission spectrum may have several peaks, and one of the larger peaks is near 253 nm. The lamp can be configured to consume less than 1 W of electric power and output about 10–50 mW of light. A parabolic reflector 222 and a lens 224 focus the ultraviolet light 226 generated by the electric discharge lamp 220. In one example, the xenon gas has a pressure of 200 mbar and the iodine gas has a pressure of 10 mbar.

An advantage of using ultraviolet light, as compared to using infrared light, is that ozone absorbs ultraviolet light at a higher rate than infrared light. This allows smaller amounts of ozone to be detected. When an electric discharge lamp containing xenon and iodine gases is used, the emission spectrum of the ultraviolet light emitted from the lamp matches well with the ultraviolet absorption spectrum of ozone molecules, which has a full width at half maximum more than 10 nm wide (e.g., between 240 nm to 270 nm), with an absorption peak near 254 nm. The absorption spectrum may have several peaks, and one of the larger peaks is near 254 nm.

An advantage of using a broadband light source (such as an electric discharge lamp or a light emitting diode), as compared to using a narrow band light source (such as a laser), is that a stronger ozone detection signal can be obtained in the presence of interfering molecules. Ozone has a broader absorption spectrum than other interfering molecules in the vicinity of 254 nm. Examples of interfering molecules are volatile aromatic compounds, whose absorption bands are often less than 1 nm. When a narrow band light source (e.g., less than 1 nm in bandwidth) is used, interfering molecules that have absorption bands overlapping the narrow light source emission band will absorb a larger portion of the light, making it difficult to determine whether the light is absorbed by ozone molecules or by interfering molecules. By comparison, when a broad band light source is used, the interfering molecules only absorb a smaller portion of the light, while a larger portion of the light is absorbed by the ozone molecules. This results in a higher signal-to-noise ratio (and higher selectivity), allowing smaller concentrations of ozone to be detected in a mixture containing interfering molecules. In one example, an ozone detector 100 using a xenon iodine electric discharge lamp having a lamp power of 20 mW can be used measure ozone concentrations as low as 10 ppbv (parts per billion in volume).

Figure 3:
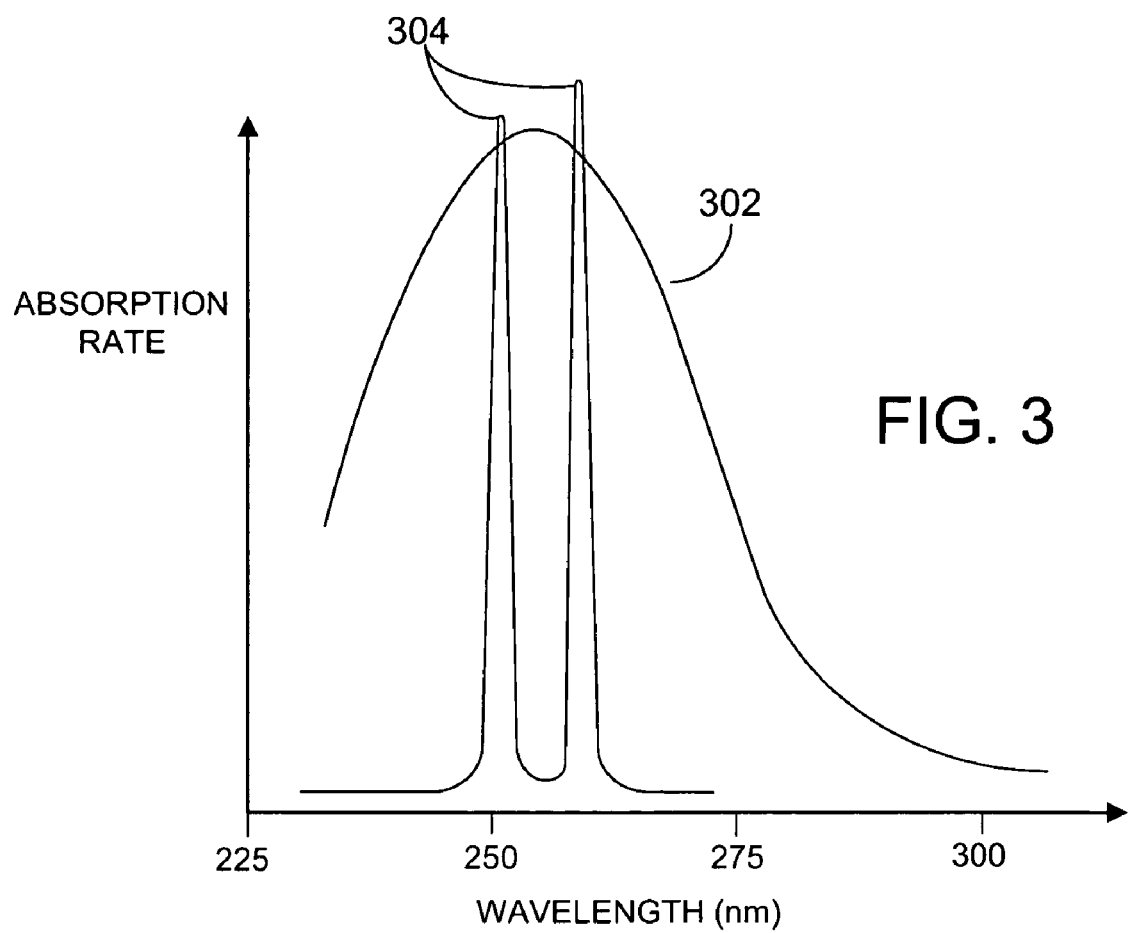
FIG. 3 depicts absorption spectrums.
Figure 4:
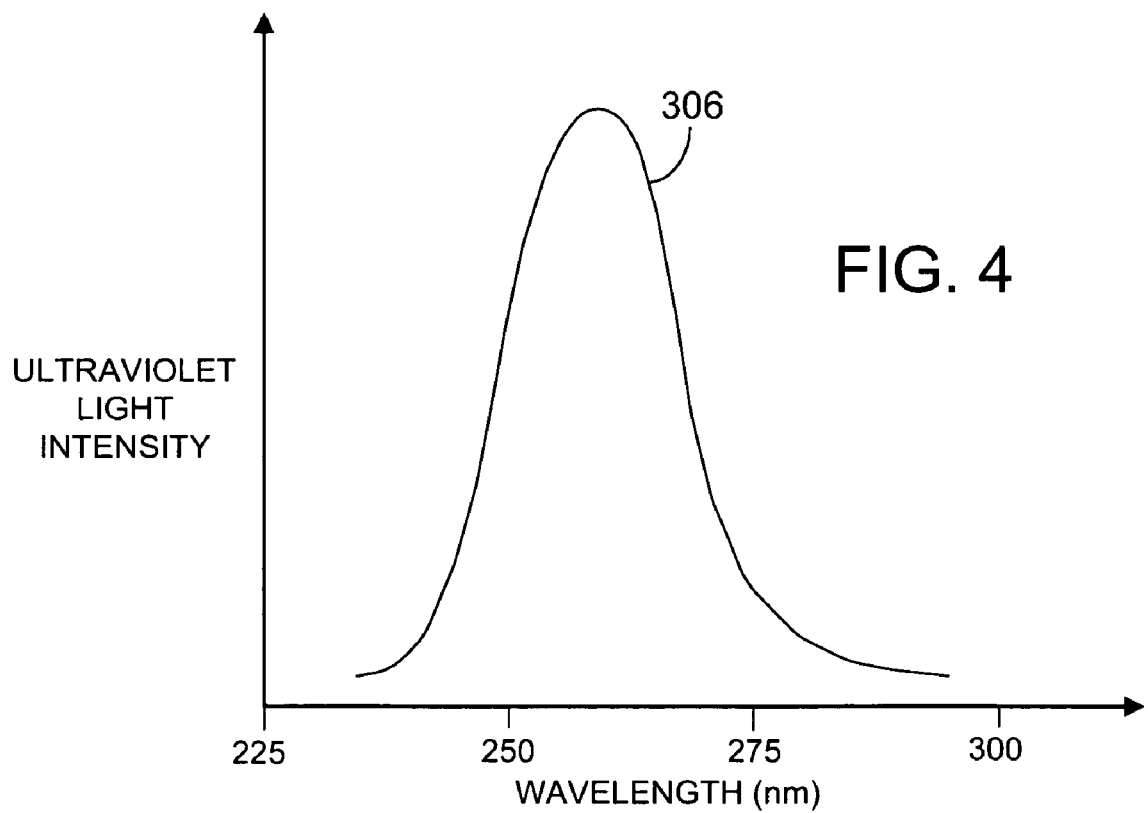
FIG. 4 depicts an emission spectrum.

As an illustration, FIG. 3 depicts an absorption spectrum 302 of ozone near 254 nm, and absorption lines 304 of interfering molecules. FIG. 4 shows an emission spectrum 306 of the broadband ultraviolet light source 102, such as an electric discharge lamp containing xenon and iodine gases. As can be seen from FIGS. 3 and 4, when a broadband light source is used, a smaller portion of the light will be absorbed by the interfering molecules, and a larger portion of the light will be absorbed by the ozone molecules. FIGS. 3 and 4 are not to scale and do not represent actual measurements; they are shown only for purpose of illustrating the working principles of the ozone detector 100.

Because the effect of volatile aromatic compounds is small, it is not necessary to use scrubbers in the detector 100 to absorb the volatile aromatic compounds. The detector 100 can be used in locations where there is smog, as the volatile aromatic compounds in the smog do not have significant effect on the detector's ability to detect ozone.

Figure 5:
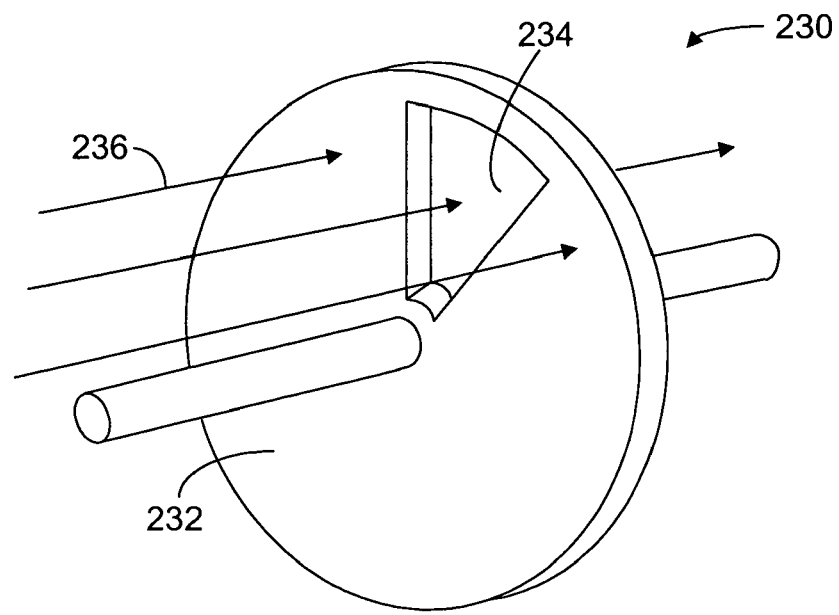
FIG. 5 depicts a light chopper.

An example of the light modulator 104 is a light chopper 230 that includes a rotatable disc 232 having an opening 234 (see FIG. 5). Ultraviolet light 236 from the light source 102 enters the photoacoustic cell 104 only when the disc 232 rotates to a position such that the opening 234 is between the light source 102 and the photoacoustic cell 104. The rotation of the disc 232 is controlled by a light chopper controller (not shown), so that the rotation frequency of the disc 232 is equal to the resonant frequency of the photoacoustic cell 104. Passing the ultraviolet light through the light chopper 230 generates a modulated ultraviolet light whose modulation frequency is equal to the resonant frequency of the photoacoustic cell 104.

The gas handling system 106 includes a sample probe, a sample inlet line, a particulate filter, solenoid valves, internal tubing, a flow meter, and a pump, which in combination brings a gas mixture to be measured (e.g., ambient air samples) to the gas inlet 112.

An ultraviolet photo-detector 110 (e.g., a photodiode) measures the amount of the ultraviolet light passing through the photoacoustic cell 104 and generates an output 118 that can be used to normalize the audio signals from the photoacoustic cell 104 which are detected by microphones 120. Output signals from the microphones 120 are sent to the signal processing system 108 through signal line 122. System 108 uses a phase-sensitive lock-in amplifier to process the audio signals to generate an output representative of the concentration of the ozone in an electronic display.

The signal processing system 108 can also be used to precisely control the modulation frequency of the light modulator 116 so that the light passing through the acoustic cell 104 has a modulation frequency equal to the resonant frequency of the acoustic cell 104, regardless of changes in the ambient environment.

The detector 100 can measure ozone concentration from 100 ppmv (parts per million in volume) to less than 10 ppbv. By comparison, naturally occurring ozone in ambient air is about 10 ppbv, and the low end of ozone concentration from common ozone generators is about 100 ppmv.

The detector 100 can be periodically calibrated with a standard concentration of ozone to ensure its accuracy.

Figure 2:
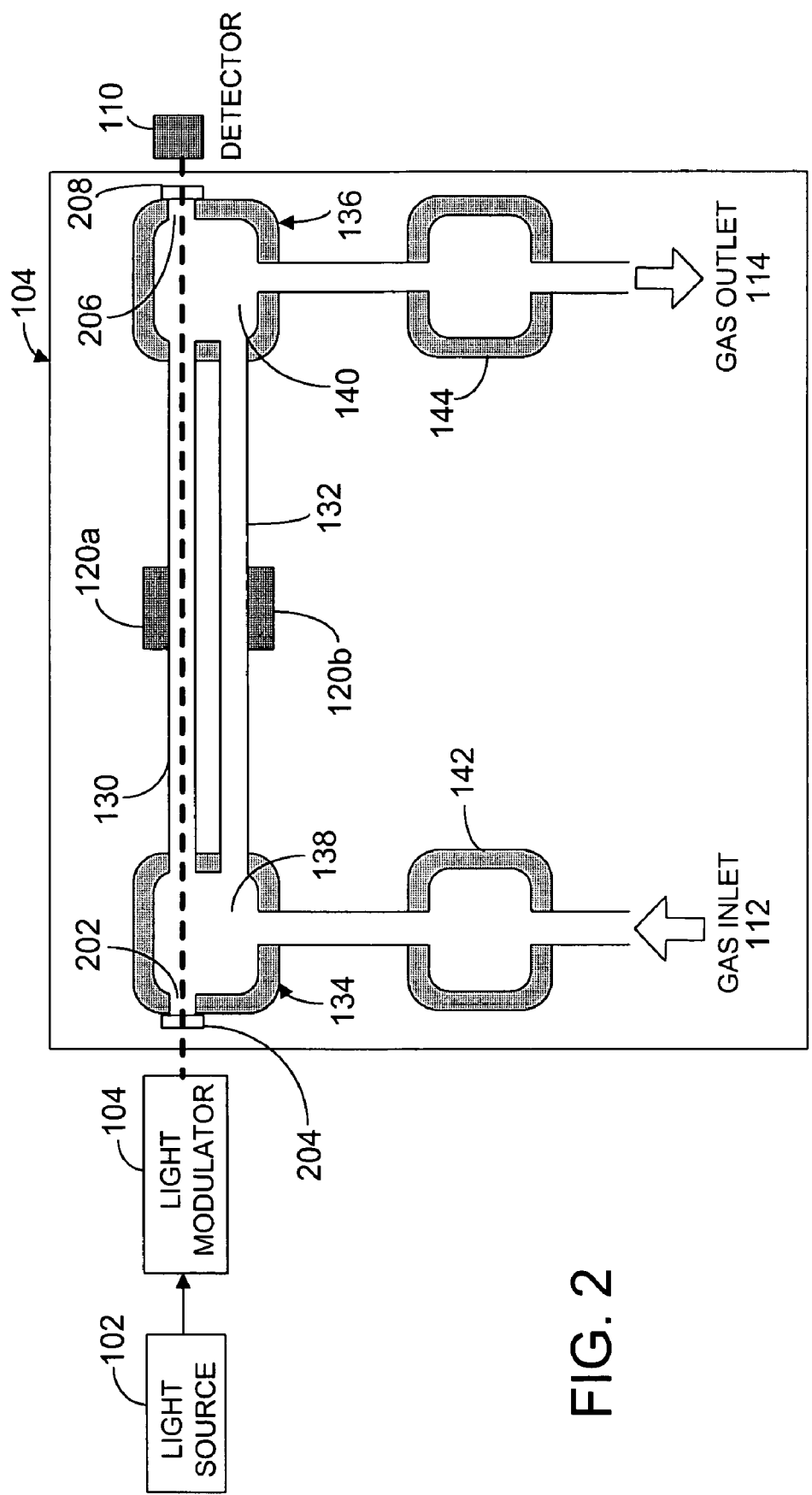
FIG. 2 depicts a photoacoustic cell.

Referring to FIG. 2, the photoacoustic cell 104 includes a pair of acoustic chambers, such as resonator tubes 130 and 132, positioned in parallel. The light from the light source 102 passes through tube 130 but not through tube 132. A microphone 120*a* is used to detect audio signals in tube 130. A microphone 120*b* is used to detect audio signals in tube 132. Both microphones 120*a* and 120*b* will detect background noise caused by turbulence gas flow. In addition, microphone 120*a* will detect audio signals caused by the modulated light being absorbed by the gas in tube 130. The outputs of the microphones 120*a* and 120*b* are sent to the signal processing system 108, which subtracts the output of microphone 120*b* from the output of microphone 120*a* and generates a detection signal representative of the absorption of the modulated light by the gas. Such differential signal processing reduces noise caused by a continuous gas flow through photoacoustic cell 104. This allows the detector 100 to be used in an environment having ambient noise.

As shown in FIG. 2, the left ends of the tubes 130 and 132 are connected to a quarter-wave acoustic filter 134, and the right ends of the tubes 130 and 132 are connected to a quarter-wave acoustic filter 136. Acoustic filter 134 has an opening 202, which is covered by a window 204 transparent to ultraviolet light. Similarly, the acoustic filter 136 has an opening 206, which is covered by a window 208 transparent to ultraviolet light. The light from the light source 102 passes window 204, opening 202, acoustic filter 134, tube 130, acoustic filter 136, opening 206, window 208, and reaches the photodetector 110.

When light passes windows 204 and 208, noise is generated due to radiation absorption by the window. Acoustic filter 134 has a buffer volume 138 designed to filter sound waves at or near the resonant frequency of the tubes 130 and 132, thereby reducing the amount of noise generated by the window 204 that reaches the microphones 120a and 120b. Acoustic filter 136 has a buffer volume 140 designed to filter sound waves at or near the resonant frequency of the tubes 130 and 132, thereby reducing the amount of noise generated by the window 208 that reaches the microphones 120a and 120b. Similarly, an acoustic filter 142 is positioned near the gas inlet 112 to filter noise from the inlet, and an acoustic filter 144 is positioned near the gas outlet 144 to filter noise from the outlet.

The length of the each of the tubes 130 and 132 is selected to be half the wavelength of the audio signal at resonant frequency. In one example, the resonant frequency is selected to be about 4 kHz. Each of the tubes 130 and 132 is configured to have a length of 40 mm and a circular cross section with a diameter of 5.5 mm. Each buffer volume of the acoustic filters has a size of about 30 mm$^3$. Depending on environment conditions, such as temperature, moisture, and gas pressure, the modulation frequency of light modulator 116 can be adjusted so that the modulation frequency is substantially equal to the resonant frequency of the tubes 130 and 132.

It is to be understood that the foregoing description is intended to illustrate and not to limit the scope of the invention, which is defined by the scope of the appended claims. Other embodiments are within the scope of the following claims.

For example, the ozone detector 100 can be modified to detect other types of gases by selecting a light source having an emission spectrum that overlaps the absorption spectrum of the type of gas being measured. In one example, by using a suitable light source, detector 100 can be used to detect sulfur dioxide ($SO_2$), which has an absorption peak near 285 nm and an absorption spectrum between 270 nm to 310 nm. In another example, by using a suitable light source, detector 100 can be used to detect nitric dioxide ($NO_2$), which has an absorption peak near 400 nm, and an absorption spectrum between 350 nm to 450 nm.

The xenon and iodine gases can have different concentrations and gas pressures. The photoacoustic cell can be configured to have different resonance frequencies. Scrubbers can be used in the gas handling system 106 when necessary. When an electric discharge lamp is used as the light source 102, other types of excimer gases, such as krypton fluoride and xenon chloride, can be used in the lamp. The light source can be a pulsed light source that emits light pulses at a frequency equal to the resonant frequency of the photoacoustic cell. In this case, it is not necessary to use the light modulator 116.

The light source 102, instead of using an electric discharge lamp, can include a diode laser that emits ultraviolet light having a wavelength of about 266 nm and a power of about 20 mW. The diode laser is selected to have a bandwidth broader than 1 nm. In this example, the detector 100 can measure ozone concentration from 100 ppmv to less than 10 ppbv. By comparison, naturally occurring ozone in ambient air is about 10 ppbv, and the low end of ozone concentration from common ozone generators is about 100 ppmv.

In FIG. 2, photoacoustic cell 104 has two resonator tubes 130 and 132. It is also possible to use a single resonator tube in a quiet environment and by reducing the flow rate of gas through the tube to reduce noise. The acoustic filters can have various sizes and shapes. The acoustic chamber(s) in the photoacoustic cell can have shapes other than tubular shapes.

What is claimed is:

1. A photoacoustic ozone detector comprising:
   an acoustic chamber having an inlet for receiving a gas mixture containing ozone and an outlet for removing the gas mixture from the chamber;
   an ultraviolet light source to generate ultraviolet light having wavelengths shorter than 400 nm, the ultraviolet light modulated at a modulation frequency substantially equal to a resonant frequency of the acoustic chamber, the ultraviolet light source positioned relative to the acoustic chamber so that the ultraviolet light passes through the gas mixture in the acoustic chamber; and
   at least one microphone to detect an audio signal in the acoustic chamber having a frequency substantially equal to the modulation frequency of the ultraviolet light;
   wherein the acoustic chamber comprises two tubes, the ultraviolet light passing through one of the tubes.

2. The photoacoustic ozone detector of claim 1 in which the ultraviolet light source is selected to have an emission spectrum with full width at half maximum greater than 1 nm.

3. The photoacoustic ozone detector of claim 1, further comprising a signal processor to generate an output indicative of a concentration of the ozone in the gas mixture based on the detected audio signal.

4. The photoacoustic ozone detector of claim 3, further comprising a photodetector to detect a level of the ultraviolet light passing through the acoustic chamber, the signal processor using the level of ultraviolet light for normalizing the output indicative of the concentration of the ozone.

5. The photoacoustic ozone detector of claim 1 in which a microphone is attached to each tube, the ozone detector further comprising a signal processor to generate an output indicative of a concentration of the ozone in the gas mixture based on a difference in the audio signals detected by the microphones.

6. The phocoacoustic ozone detector of claim 1 which the ultraviolet light source comprises an electric discharge lamp.

7. The photoacoustic ozone detector of claim 6 in which the electric discharge lamp comprises xenon gas and iodine gas.

8. The photoacoustic ozone detector of claim 1 in which the ultraviolet light source generates ultraviolet light having wavelengths between 240 mn to 270 nm.

9. The photoacoustic ozone detector of claim 1 which the acoustic chamber is selected to have dimensions so that the resonant frequency is between 100 Hz to 40 kHz.

10. The photoacoustic ozone detector of claim 1, further comprising an acoustic filter attached to the acoustic chamber to reduce background noise having a frequency substantially equal to the modulation frequency of the light emitted from the light source.

11. The photoacoustic ozone detector of claim 1, further comprising a gas handling system to supply the gas mixture.

12. A photoacoustic ozone detector comprising:
   an acoustic chamber having an inlet for receiving a gas mixture containing ozone and an outlet for removing the gas mixture from the chamber;
   an ultraviolet light source to generate ultraviolet light having wavelengths shorter than 400 nm, the ultraviolet light modulated at a modulation frequency substantially equal to a resonant frequency of the acoustic chamber, the ultraviolet light source positioned relative to the acoustic chamber so that the ultraviolet light passes through the gas mixture in the acoustic chamber; and at least one microphone to detect an audio signal in the acoustic chamber having a frequency substantially equal to the modulation frequency of the ultraviolet light;

wherein the acoustic chamber has two ends, each coupled to an acoustic filter to reduce background noise having a frequency substantially equal to the resonant frequency.

13. The photoacoustic ozone detector of claim 12 in which the acoustic filter comprises a quarter wavelength acoustic filter.

14. The photoacoustic ozone detector of claim 12 in which the ultraviolet light source is selected to have an emission spectrum with full width at half maximum greater than 1 nm.

15. The photoacoustic ozone detector of claim 12, further comprising a signal processor to generate an output indicative of a concentration of the ozone in the gas mixture based on the detected audio signal.

16. The photoacoustic ozone detector of claim 15, further comprising a photodetector to detect a level of the ultraviolet light passing through the acoustic chamber, the signal processor using the level of ultraviolet light for normalizing the output indicative of the concentration of the ozone.

17. The photoacoustic ozone detector of claim 12 in which the ultraviolet light source comprises an electric discharge lamp.

18. The photoacoustic ozone detector of claim 17 in which the electric discharge lamp comprises xenon gas and iodine gas.

19. The photoacoustic ozone detector of claim 12 in which the ultraviolet light source generates ultraviolet light having wavelengths between 240 nm to 270 nm.

20. The photoacoustic ozone detector of claim 12 in which the acoustic chamber is selected to have dimensions so that the resonant frequency is between 100 Hz to 40 kHz.

21. The photoacoustic ozone detector of claim 12, further comprising a gas handling system to supply the gas mixture.

* * * * *